United States Patent [19]

Regenstein, Jr.

[11] 4,402,453

[45] Sep. 6, 1983

[54] POUCH WITH CLOSURE SEAL STRIP AND METHOD FOR MAKING SAME

[75] Inventor: Joseph R. Regenstein, Jr., Chicago, Ill.

[73] Assignee: Arvey Corporation, Chicago, Ill.

[21] Appl. No.: 277,111

[22] Filed: Jun. 25, 1981

[51] Int. Cl.³ .............................................. B65D 33/16
[52] U.S. Cl. ..................................... 229/62; 206/813; 206/439; 206/484; 229/48 SB; 229/90
[58] Field of Search ............... 206/439, 633, 813, 484; 229/62, 48 SB, 90

[56] References Cited

U.S. PATENT DOCUMENTS

| | | | |
|---|---|---|---|
| 3,070,280 | 12/1962 | Richmond | 229/80 |
| 3,149,771 | 9/1964 | Pearl | 229/48 SB |
| 3,245,607 | 4/1966 | Kelson | 229/62 |
| 3,655,118 | 4/1972 | Rinecker | 229/62 |
| 3,702,171 | 11/1972 | Levine | 229/90 |
| 4,084,689 | 4/1978 | Yamagata | 206/280 |
| 4,288,279 | 9/1981 | Blore et al. | 156/498 |

FOREIGN PATENT DOCUMENTS 2927465 7/1980 Fed. Rep. of Germany .
507845 7/1971 Switzerland .

Primary Examiner—William T. Dixson, Jr.
Attorney, Agent, or Firm—Dressler, Goldsmith, Shore, Sutker & Milnamow, Ltd.

[57] ABSTRACT

A pouch and method for making a pouch are disclosed wherein the pouch comprises first and second webs secured together at least partially around an interior portion of the webs and wherein a sealing strip extends across the pouch. The sealing strip has a carrier member with a first portion secured to the first web and with an unsecured second portion. Adhesive is provided on the second portion of the carrier member and the second portion is covered with a release paper which can be removed so that the carrier member can be secured over the pouch opening by adhering the carrier member second portion to the second web to form a closure seal at the pouch opening.

20 Claims, 41 Drawing Figures

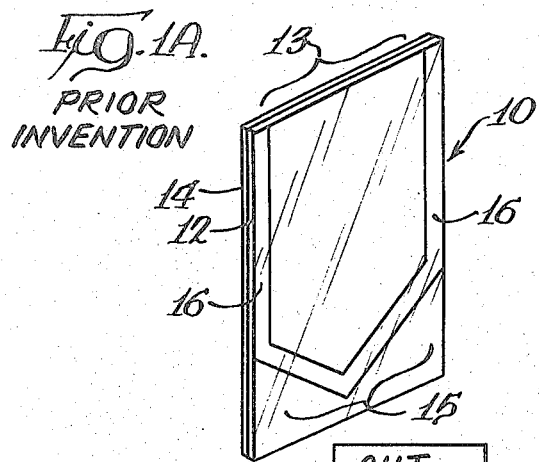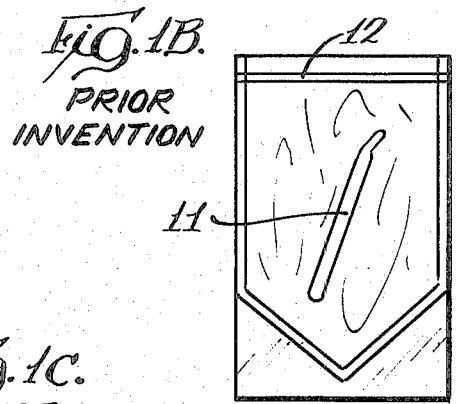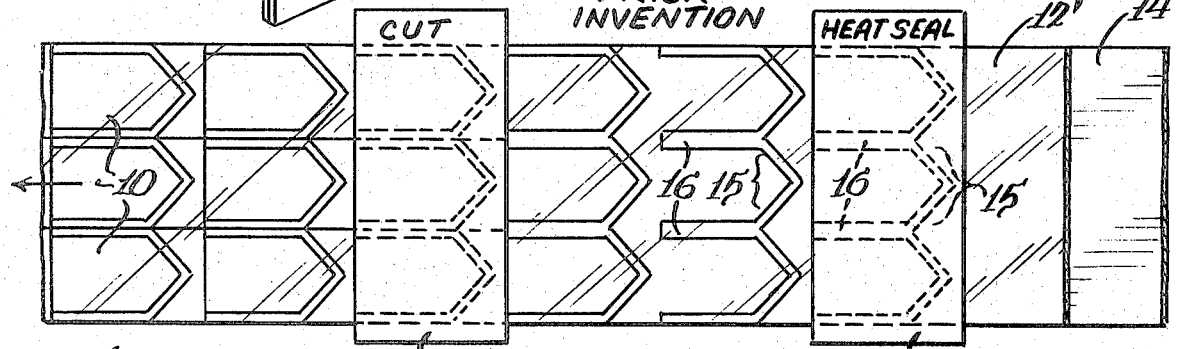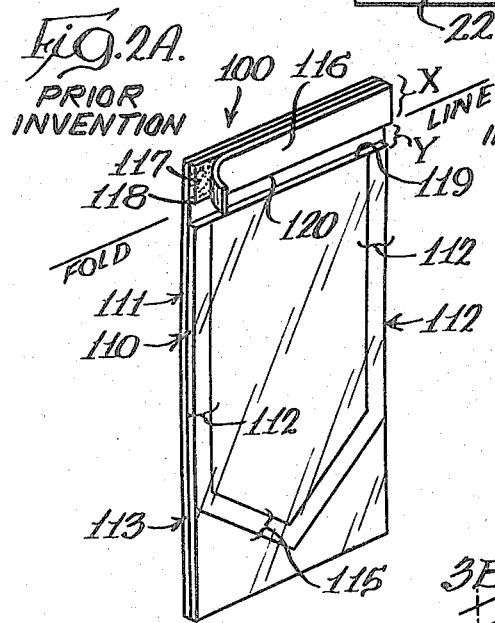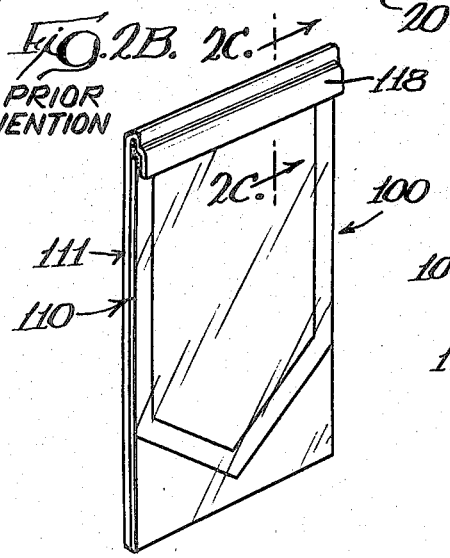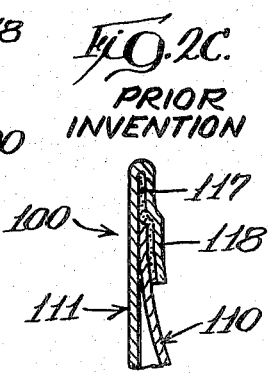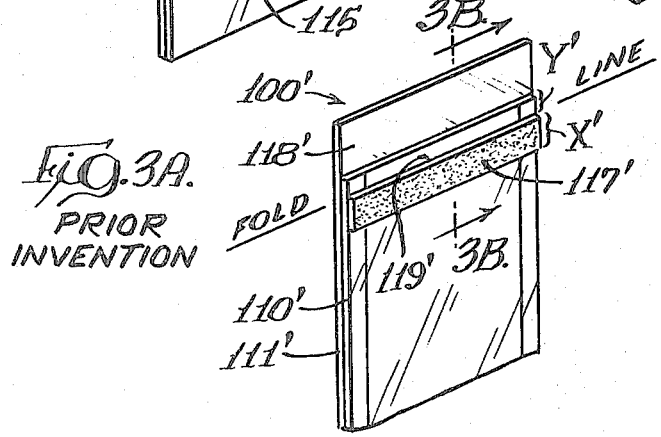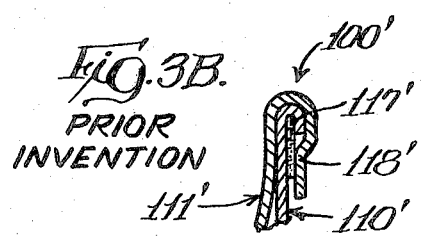

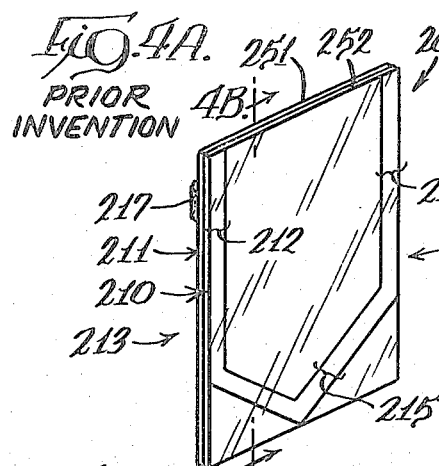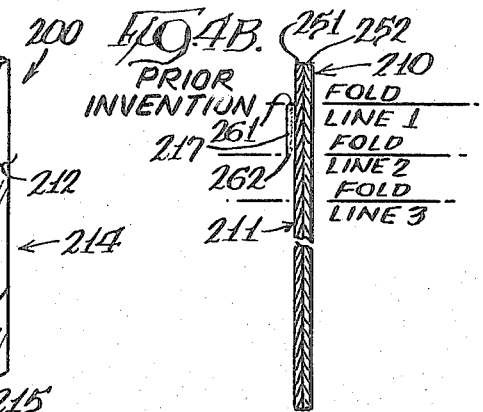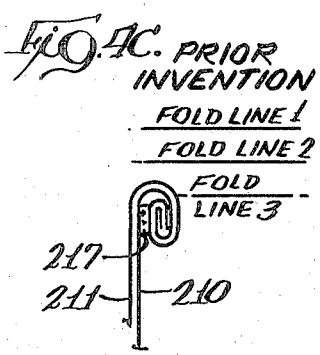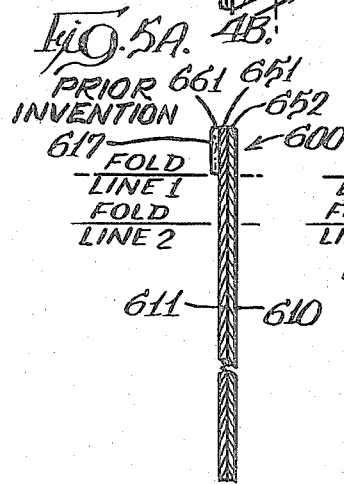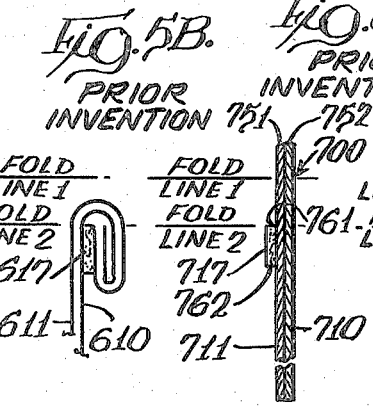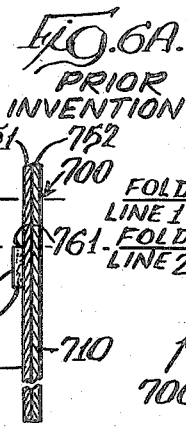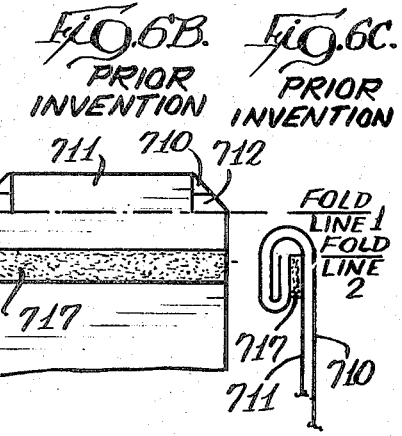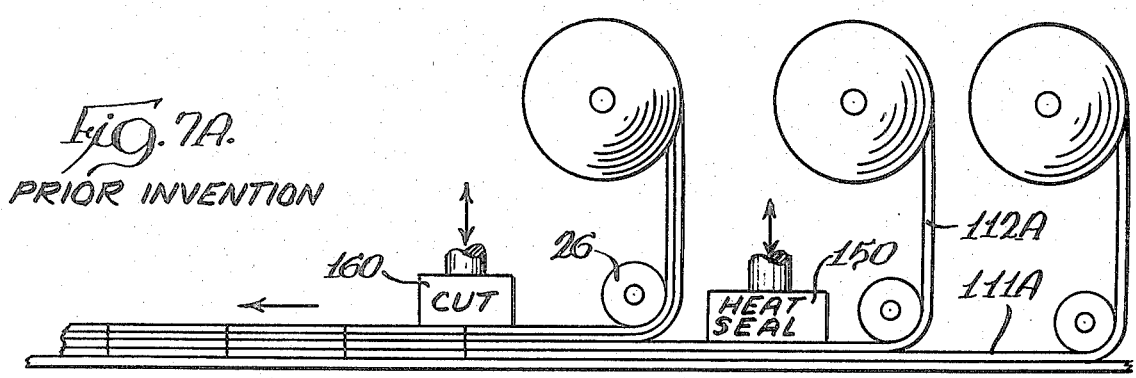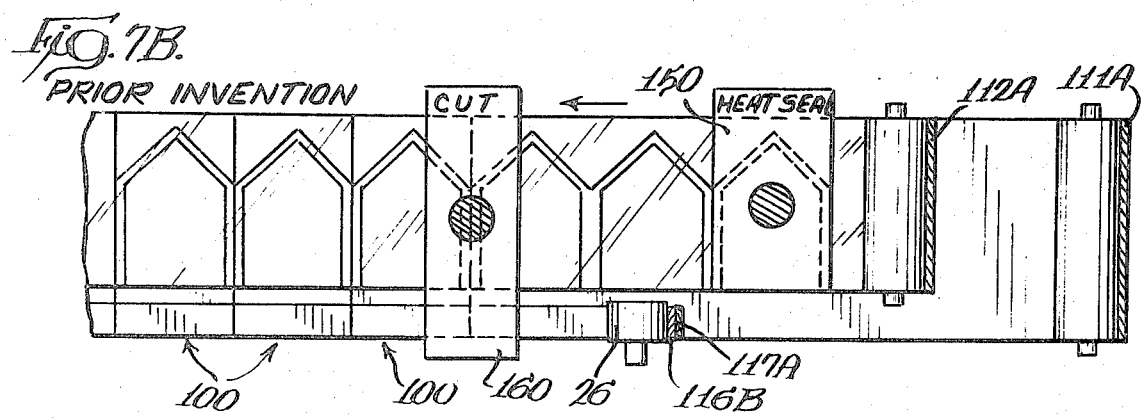

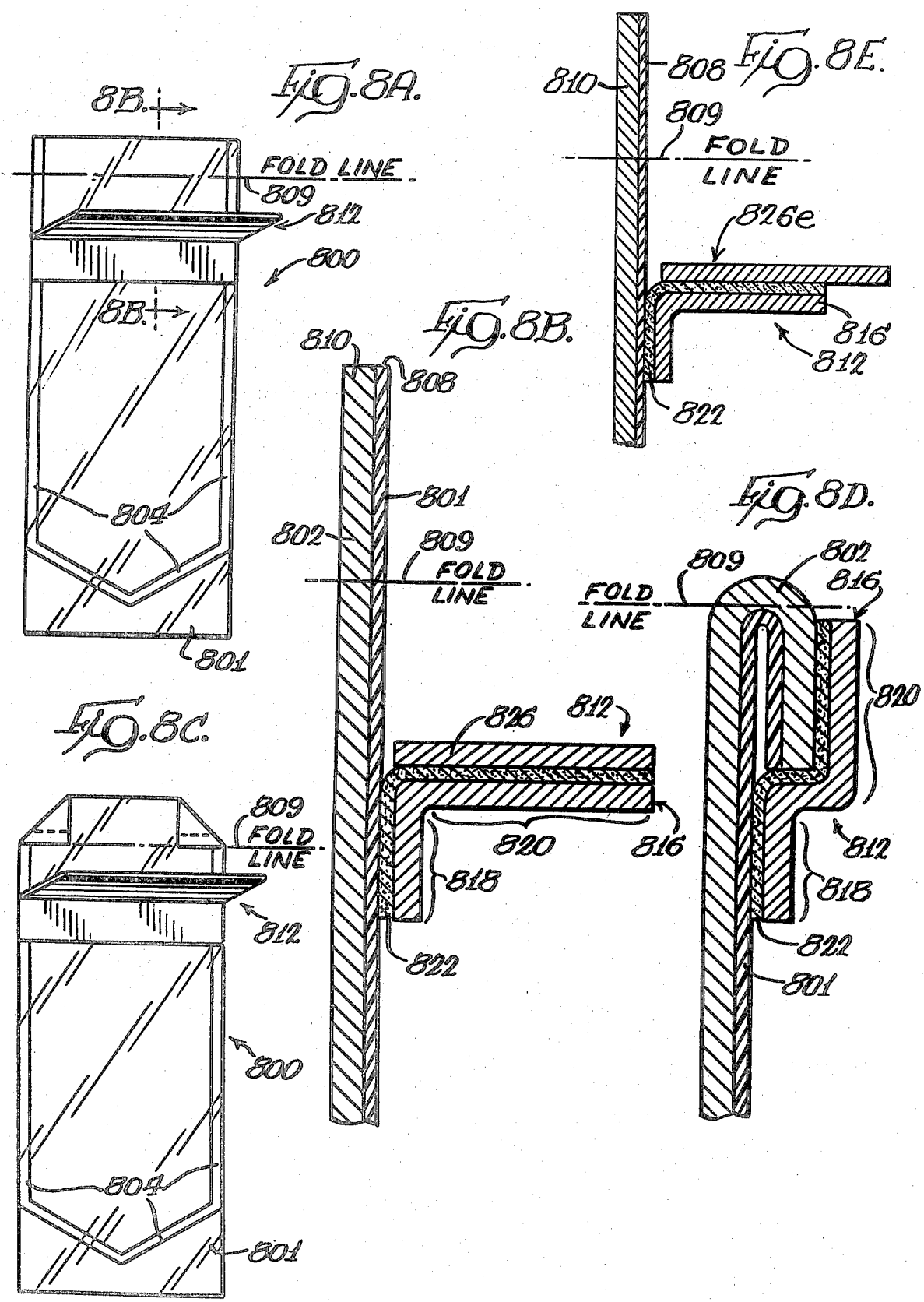

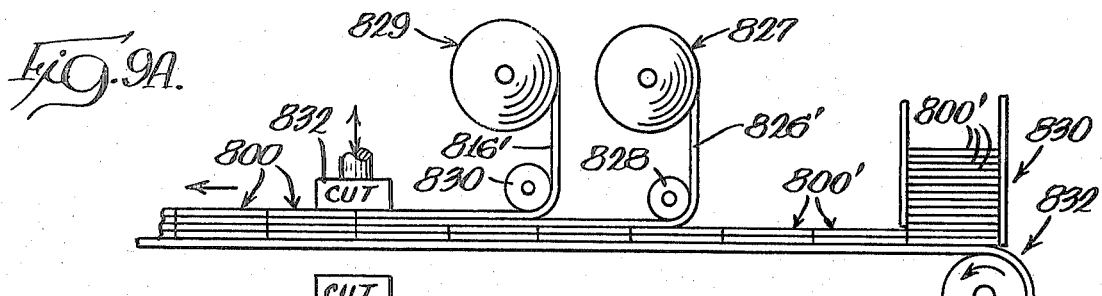
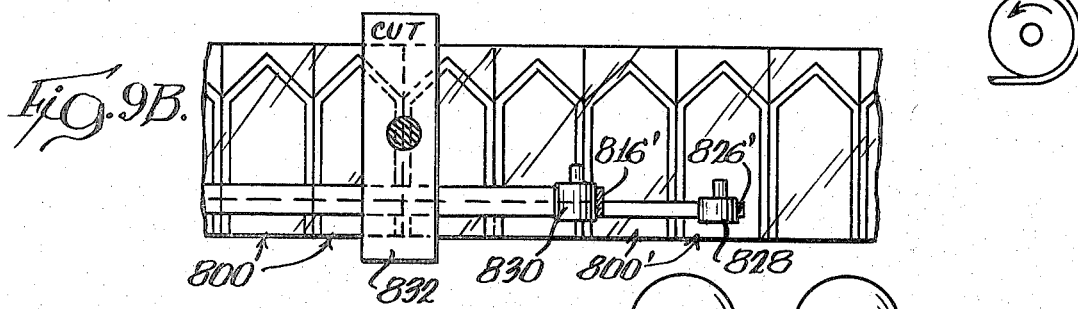
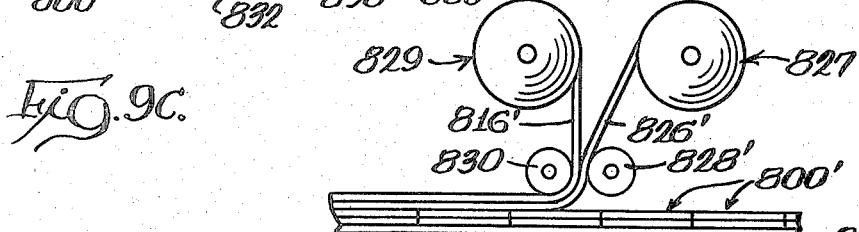
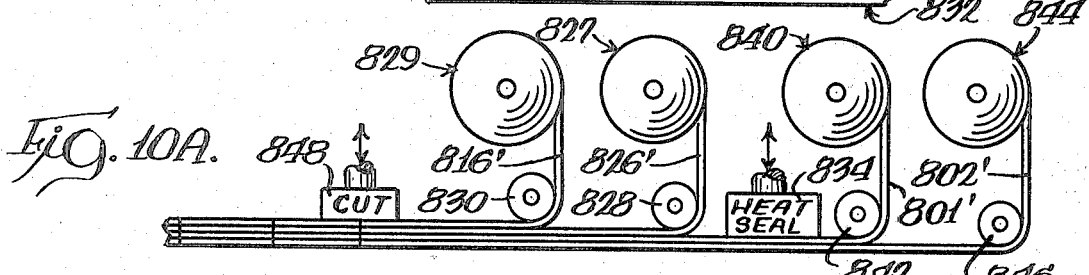
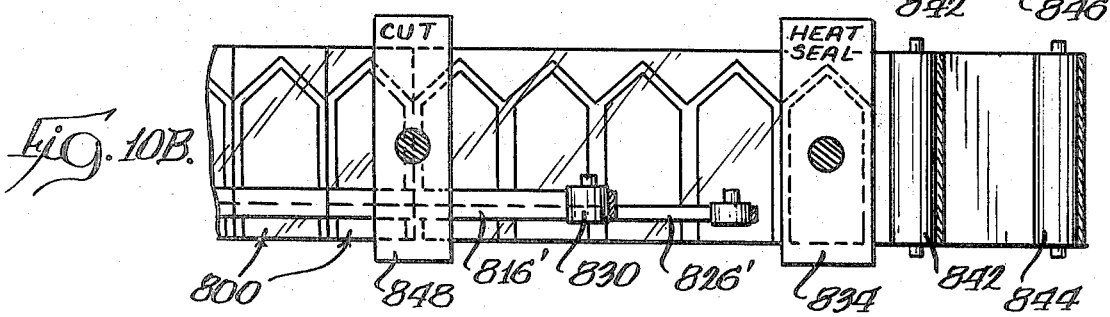
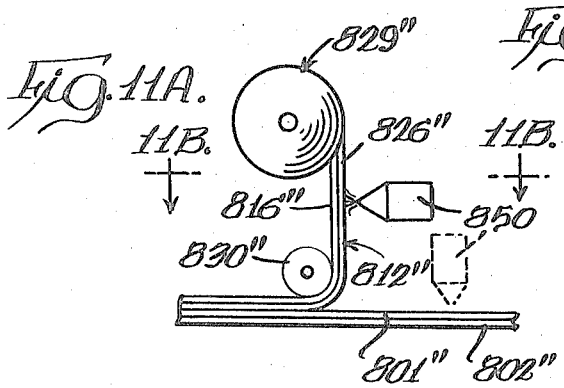
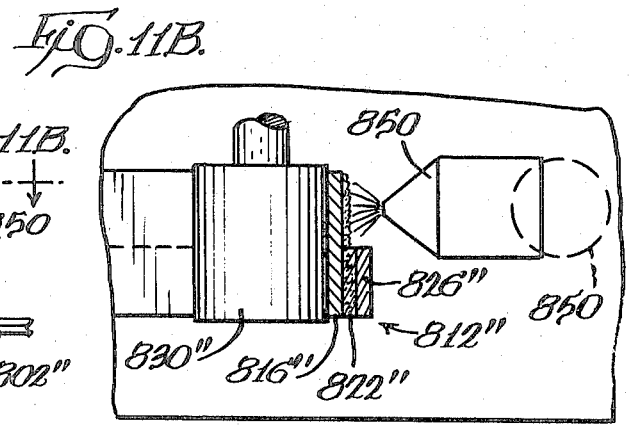

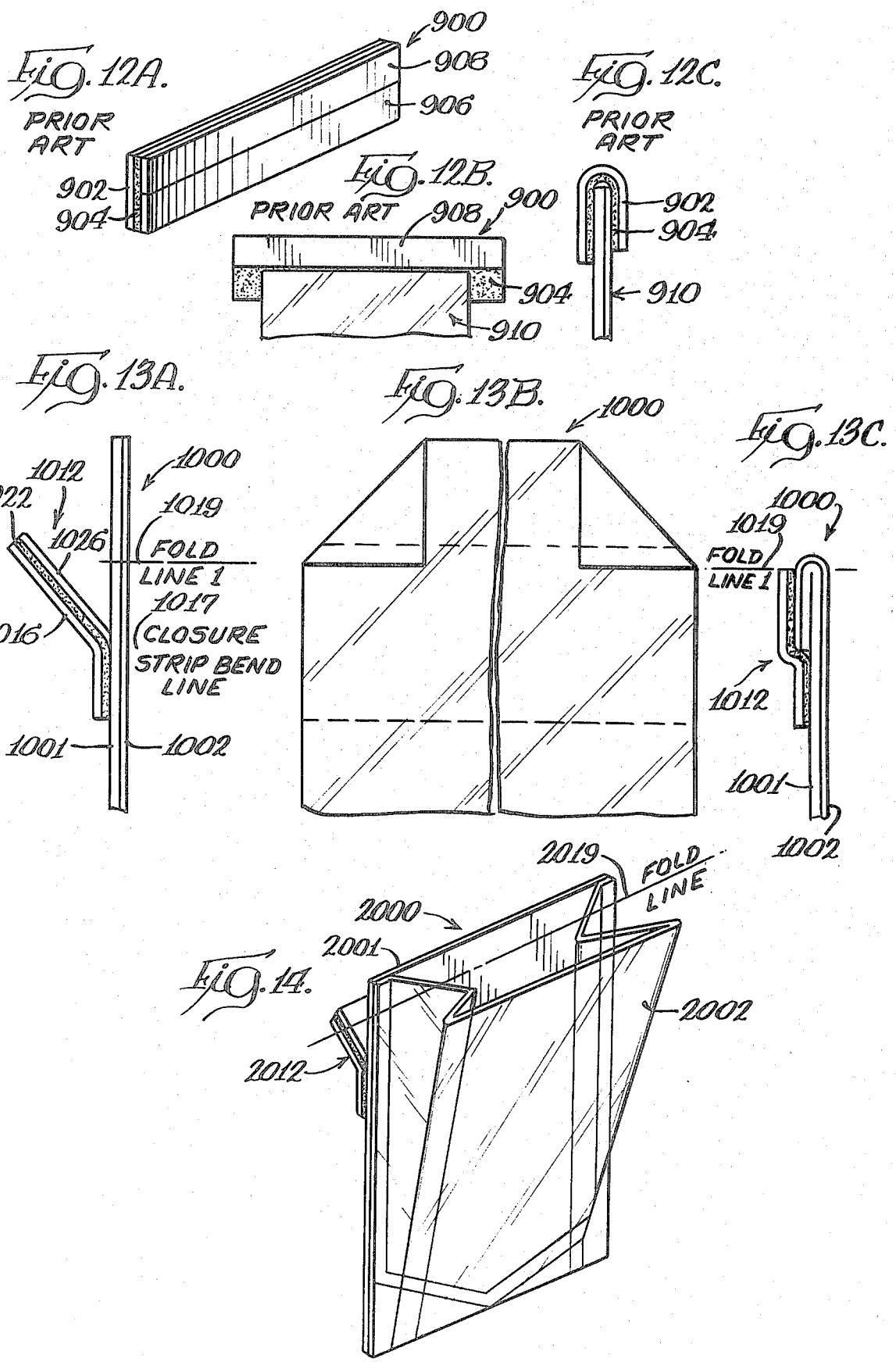

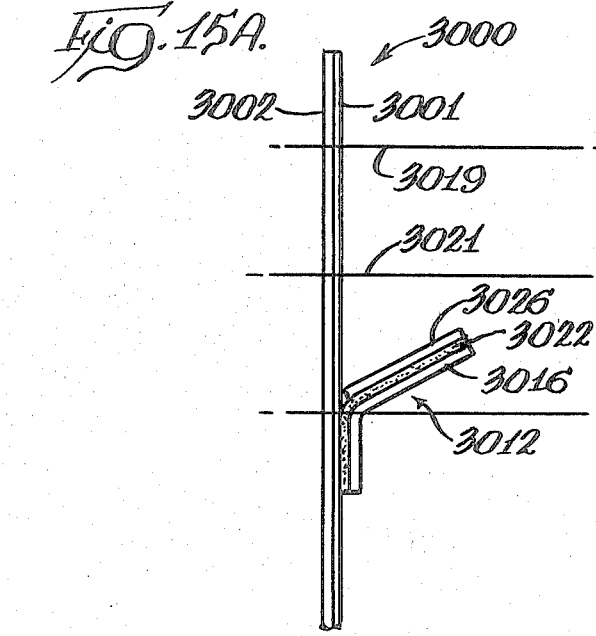
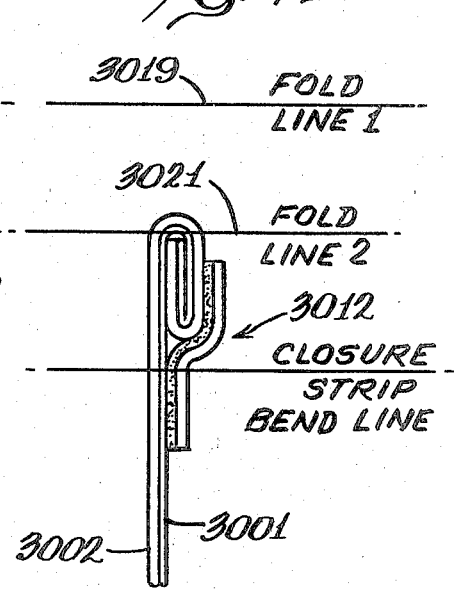
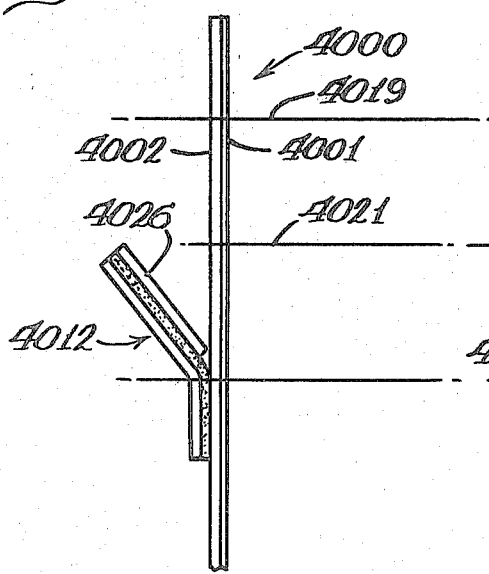
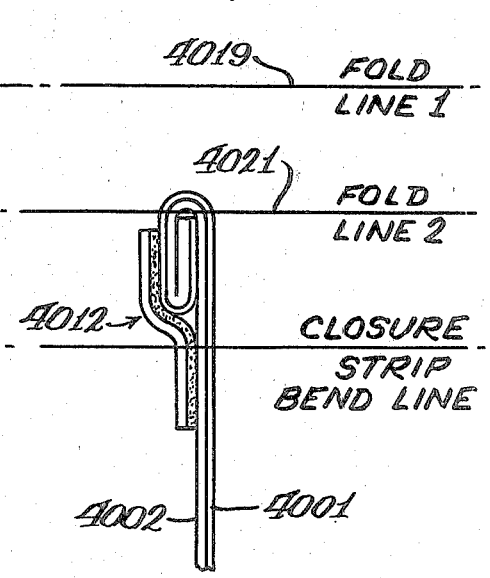

POUCH WITH CLOSURE SEAL STRIP AND METHOD FOR MAKING SAME

DESCRIPTION

1. Technical Field

The present invention relates to disposable pouches. The present invention finds greatest application in the medical field wherein sterilizable pouches are used with sterilizable patient care articles. More particularly, the present invention is directed to a pouch having a self-sealing closure strip and to a method for making such a pouch.

2. Background of the Invention

There have been a substantial number of containers, bags and pouches developed over the years in which the pouch opening can be closed. Examples of such pouches are disclosed in the U.S. Pat. Nos. Re. 28,318; 2,339,304; 3,070,280; 3,245,607; 3,420,433; 3,363,828; 4,084,689; West German Offenlegungsschrift No. 25 18 229, and Belgian Pat. No. 548933.

The pouches disclosed in some of the above-identified patents comprise first and second opposing webs secured together partially around an interior portion of the webs. In some such pouches, the pouch webs are coextensive and the web ends are in registry at the pouch opening. Such a pouch may be sealed at the opening with a conventional heat seal by conventional techniques.

Such heat sealable pouches are typically fabricated in a continuous manner. Typically, the two webs forming a pouch are drawn off of rolls and fed together in registry along a path. The pouches are initially formed in the webs by intermittently heat sealing the webs together to form the sides and bottom of the pouches.

Typically, a plurality of the above-described heat-sealable pouches are initially formed across the width of the moving webs, leaving the webs unsealed across the openings of the pouches. The openings across the width of the pouches are thus oriented generally normal to the direction of movement of the two webs. The two webs forming the pouches may then be cut through by suitable means to form the individual pouches. When pouches are fabricated thusly, it is obviously not possible to provide a pouch structure wherein one of the webs has a portion of flap extending beyond the edge of the other web at the pouch opening. However, such a method of forming heat sealable pouches is highly efficient in that long pouches can be formed with a plurality of such long pouches disposed across the widths of the web.

Another type of pouch has a portion or flap extending on one of the webs beyond the edge of the other web at the pouch opening. This type of pouch is easily adapted to be provided with a self-closure sealing strip so that the opening across the width of the pouch can be closed by means of an adhesive strip without the use of a separate heat sealing operation. The adhesive strip may be initially covered with a release paper. The release paper may be slit along its length to facilitate removal. Pouches with extending flaps cannot be fabricated on a continuous basis with the edges of the pouch openings across the widths of the pouches being oriented generally normal to the direction of movement of the webs. Such pouches must instead be fabricated on a continuous basis from two webs with the pouches oriented so that the edges of the pouch openings across the widths of the pouches are parallel to the direction of movement of the webs.

In particular, since one of the webs has a width less than that of the other web, the webs are fed together in a path with the longitudinal edges of the two webs in registry on one side and with the wider of the two webs extending beyond the narrower of the two webs on the other side. Then the pouches are intially formed in the webs by heat sealing the webs together to form the sides and bottoms of the pouches. Downstream of the heat sealing operation, a continuous length of adhesive sealing strip is typically applied to the extending portion of the wider web. The sealing strip has an upwardly facing adhesive which is typically covered with a removable release paper. Downstream of the point of application of the adhesive sealing strip to the pouches, the webs are severed to form the individual pouches with the self-closure sealing strip secured thereto. The extending portion or flap of the formed pouch may then be folded down over the pouch opening and secured with the adhesive strip on the other web.

It would be desirable to provide a pouch having an opening defined by coextensive edges of each of the two webs but which could be provided with a self-closure seal for effective securement and sealing of the pouch opening when the pouch is closed. Such a pouch, with coextensive web edges at its opening, could then be fabricated on a continuous basis with the pouch oriented so that the opening was generally normal to the direction of the feeding of the webs. This would permit a plurality of long pouches to be fabricated in side-by-side relationship across the width of the webs.

Further, it would be desirable to provide an efficient method for applying the self-closure sealing strip in a separate operation after the pouches had been made by the highly efficient method described above.

SUMMARY OF THE INVENTION

A pouch is defined by first and second opposing webs secured together at least partially around an interior portion of the web. The first web has at least one generally straight end edge defining a part of the pouch opening and the second web has at least one generally straight end edge oriented generally parallel to and in registry with the first web one end edge. The second web is unsecured to the first web at the end edges to define the opening.

A sealing strip is provided across the pouch and includes a carrier member having a first portion secured to the first web and having an initially unsecured second portion. The unsecured second portion of the carrier member is covered or coated with an adhering means or adhesive for ultimately adhering to the second web. However, initially a removable cover means is provided on the carrier member over the adhering means on the second portion of the carrier member for preventing the second portion of the carrier member from adhering to either of the webs unless the cover means is removed.

In use, the webs are folded over together about at least one fold line defined across the webs between the first web one end edge and the carrier member first portion. Then the cover means is removed and the carrier member second portion is then adhesively secured to the folded portion of the second web to form a closure seal at the pouch opening.

A method is provided for securing the sealing strip to the pouches. Specifically, the previously formed pouches are fed along a path in side-by-side relationship with an open end of each pouch oriented generally parallel with the direction of feeding movement. Tape with adhesive means on one side surface is fed in the path adjacent the pouches with the adhesive means facing the pouches. A cover strip having a width less than the width of the tape is fed along the path between the tape and the pouches with one edge of the cover strip aligned with one edge of the tape. The tape and cover strip are moved or urged together to adhere the cover strip to the tape. The tape is also moved or urged against the pouches to adhere the tape to the pouches. Finally, the adhered tape and cover strip are transversely severed between the pouches to produce individual pouches with attached self-closure sealing strips.

In another embodiment of the method, the tape and narrower cover strip may be fed adjacent the continuous webs of material in which the pouch openings are oriented generally parallel to the direction of movement of the webs. With this arrangement, the tape and cover strip can be secured to the webs forming the pouches before the individual pouches are separated.

Numerous other advantages and features of the present invention will become readily apparent from the following detailed description of the invention and of embodiments thereof, from the claims and from the drawings.

BRIEF DESCRIPTION OF THE DRAWINGS

In the accompanying drawings forming part of the specification and in which like numerals are employed to designate like parts throughout the same, FIG. 1A is a perspective view showing an unsealed, by heat sealable, pouch of prior invention;

FIG. 1B is the pouch of FIG. 1A with an article received within the pouch that has been closed with a heat seal;

FIG. 1C is a simplified, schematic illustration of the method of making the pouch of FIG. 1A;

FIG. 2A is a front perspective view of a second pouch of prior invention is an unsealed condition;

FIG. 2B is the second pouch of FIG. 2A shown sealed closed;

FIG. 2C is an enlarged, fragmentary cross-sectional view taken generally along the plane 2C—2C in FIG. 2B;

FIG. 3A is a fragmentary, front perspective view of a third unsealed pouch of prior invention;

FIG. 3B is an enlarged, fragmentary, cross-sectional view taken generally along the plane 3B—3B in FIG. 3A, but with the flap portion of the pouch folded and sealed;

FIG. 4A is a front, perspective view showing a fourth unsealed pouch of prior invention;

FIG. 4B is a fragmentary, cross-sectional view taken generally along the plane 4B—4B in FIG. 4A;

FIG. 4C is a simplified, schematic diagram illustrating the folding of one end of the pouch of FIGS. 4A and 4B to form a seal at the open end thereof;

FIG. 5A is an enlarged, fragmentary, cross-sectional view of a fifth embodiment of an unsealed pouch of prior invention;

FIG. 5B is a simplified, schematic diagram illustrating the folding of the open end of the pouch of FIG. 5A to form a seal;

FIG. 6A is a fragmentary, cross-sectional view of a sixth embodiment of a pouch of prior invention;

FIG. 6B is a fragmentary, plan view of the pouch of 6A showing the open end corners folded over;

FIG. 6C is a simplified, schematic diagram illustrating the folding closure seal of the pouch of FIGS. 6A and 6B;

FIG. 7A is a simplified, schematic diagram illustrating the method of manufacturing the second embodiment of the pouch illustrated in FIG. 2A;

FIG. 7B is a simplified, schematic plan view of the method illustrated in FIG. 7A;

FIG. 8A is a view of a first embodiment of the novel pouch in accordance with the teachings of the present invention;

FIG. 8B is a greatly enlarged, fragmentary, cross-sectional view taken generally along the plane 8B—8B in FIG. 8A;

FIG. 8C is a plan view of the pouch of FIG. 8A, but showing the corners folded prior to forming the complete closure seal;

FIG. 8D is an enlarged, fragmentary, cross-sectional view of the pouch shown in FIGS. 8A, 8B, and 8C, but with the pouch folded, closed and sealed;

FIG. 8E is an enlarged, fragmentary, cross-sectional view similar to FIG. 8B and showing the same pouch construction except that an alternate embodiment of the cover member is illustrated as extending outwardly beyond the end edge of the sealing strip;

FIG. 9A is a simplified, schematic view illustrating a method for applying a self-closure sealing strip to form the pouch illustrated in FIGS. 8A-8D;

FIG. 9B is a simplified, schematic plan view diagram of the method illustrated in FIG. 9A;

FIG. 9C is a simplified, schematic view similar to FIG. 9A but illustrating a modification of the method illustrated in FIG. 9A;

FIG. 10A is a simplified, schematic diagram illustrating a method of forming the pouch of FIGS. 8A-8D on a continuous line and applying the sealing strip thereto in the same continuous line;

FIG. 10B is a simplified, schematic plan view diagram of the method illustrated in FIG. 10A;

FIG. 11A is a simplified, schematic diagram illustrating a modification of the methods illustrated in FIGS. 9A, 9B, 9C, 10A, and 10B;

FIG. 11B is a greatly enlarged, fragmentary, cross-sectional view taken generally along the plane 11B—11B in FIG. 11A;

FIG. 12A is a perspective view of a prior art sealing device for a pouch;

FIG. 12B is a fragmentary view showing the sealing device of FIG. 12A being applied to a pouch;

FIG. 12C is a fragmentary, enlarged, cross-sectional view of the sealing device of FIG. 12A closed over the end of a pouch;

FIG. 13A is a fragmentary, side view of a further modification of the pouch in accordance with the teachings of the present invention;

FIG. 13B is a fragmentary, front view of the pouch illustrated in FIG. 13A but showing the corners folded over as one step in the closure process;

FIG. 13C is a view similar to FIG. 13A but showing the pouch folded and sealed;

FIG. 14 is a front, perspective view of another type of pouch, a gusseted pouch, having a closure strip structure similar to that illustrated for the pouch in FIG. 13A;

FIG. 15A is a fragmentary, side view of a further embodiment of the pouch in accordance with the teachings of the present invention;

FIG. 15B is a view similar to FIG. 15A but showing the pouch folded and sealed;

FIG. 16A is a fragmentary, side view of another form of a pouch in accordance with the teachings of the present invention; and FIG. 16B is a view similar to FIG. 16A but showing the pouch folded and sealed.

DETAILED DESCRIPTION

Prior Inventions

With reference to FIG. 1A, a pouch of prior invention is designated therein generally by the reference numeral 10. The pouch includes first and second webs of material 12 and 14, respectively, which are placed together to form the walls of the pouch having an openable end 13, a permanently heat sealed end 15, and heat sealed side margins 16.

Pouches of this type are well known and in commercial use. Typically, the first web 12 is a transparent, thermally stable material such as a coated or laminated polyethylene terephthalate. The second web 14 is typically a steam permeable paper that permits the pouch 10 to undergo autoclave sterilization.

As illustrated in FIG. 1B, an article 11 to be sterilized may be inserted in the pouch. Then the two webs 12 and 14 are heat sealed, as at heat seal 12 by suitable conventional heat sealing apparatus (not illustrated).

As best illustrated in FIG. 1C, a plurality of pouches 10 may be fabricated in a continuous line process. Specifically, a sheet of material 12' used for forming the pouch first web 12 is fed along a path adjacent, and in registry with, a sheet of material 14' used for forming the pouch second web 14.

The feeding of the webs or sheets 12' and 14' is intermittently interrupted to permit the sheets to be sealed together by a suitable conventional heat sealing apparatus 20 to form the seals at the bottom end 15 of each pouch and to form the side seals 16. Such heat sealing apparatus 20 could also include hot roller devices that would permit the sheets 12' and 14' to be continuously fed. In either case, such heat sealing apparatus 20 is well known to those skilled in the art and the details of such heat sealing apparatus 20 form no part of the present invention.

As best illustrated in FIG. 1C, the sheets 12' and 14', with the formed pouch heat seals 16 and 15, are fed to a cutting apparatus 22 which severs the sealed webs in the desired configuration around the heat seals to provide the individual pouches 10.

It is to be noted that, in the conventional method for fabricating the pouches 10 as illustrated in FIG. 1C, a plurality of such pouches may be formed across the width of the webs or sheets 12' and 14'. Typically, the sheets 12' and 14' are between 20 and 40 inches in width and two or more pouches 10 may be formed in side-by-side relationship across the width of the sheets.

Another pouch known to the inventor of the present invention is that designated generally by the reference numeral 100 in FIGS. 2A, 2B and 2C. The pouch 100 preferably comprises two opposing webs, first web 111 and second web 110, which have an open end defined between a pair of side heat seals 112 and which are sealed with a bottom heat seal structure 115. Typically, the first web 111 is a steam or gas permeable paper and the second web 112 is a coated or laminated polyethylene terephthalate.

At the open end of the pouch 100, the first web 111 extends therefrom as a flap 118. An adhesive 117 is applied across the surface of the flap 118. The adhesive 117 has a width X and is spaced a distance Y from an upper unsealed lip 119 of the web 110. The distance Y and the width X are suitably related so that the width of the adhesive 117 is broad enough to cover an area adjacent each side of lip 119 when the flap 118 is folded to form a continuous seal and prevent contamination of the contents of the pouch after sterilization.

Typically, a removable cover member or conventional release paper 116 is provided over the adhesive 117 and is removed immediately prior to closing the pouch 100. The release paper 116 prevents premature adherence of the adhesive 117 to other materials that may be accidentally placed against the pouch 100. To this end, the release paper 116 is of conventional design and can be peeled away from the adhesive 117 without peeling the adhesive 117 from the extending flap portion 118 of the pouch.

FIG. 2B shows the prior invention pouch 100 of FIG. 2A in the closed or sealed position. The closure of the pouch 100 is obtained by folding the flap 118 along the fold line generally defined by the adhesive strip bottom margin or edge 120. The margin 120 is the edge of the adhesive strip that is nearest the lip 119. The flap 118 is folded over and this essentially seals the web 111 to itself and also to the area of the web 110 as is illustrated best in FIG. 2C.

Another embodiment of a prior invention pouch 100', similar to the pouch 100 illustrated in FIGS. 2A, 2B, and 2C, is illustrated in FIGS. 3A and 3B. Here a pressure sensitive adhesive strip 117' is disposed on the outer surface of a web 110' rather than on the inner surface of a web 111'.

The adhesive strip 117' has a width X' and is spaced a distance Y' from the lip 119' of the web 110'. The distance Y' and the width X' of the adhesive are cooperatively selected to provide a contaminant proof seal. The closure of the pouch 100' illustrated in FIG. 3A is made by folding the pouch along a fold line generally defined by the edge of the adhesive 117' nearest the lip 119'. The closed pouch is illustrated in FIG. 3B where it may be seen that the film web 110' is sealed to itself and to the flap 118' of the web 111' to form a contaminant proof seal.

FIGS. 4A, 4B and 4C illustrate another pouch of prior invention wherein the pouch is designated generally by the reference numeral 200. The pouch 200 has an opposing web structure similar to the web structure of the prior invention pouches described above.

Basically, the pouch 200 has a first, or base web 211, which may be made of a steam permeable paper to permit the pouch to undergo autoclave sterilization, and a second, or top web 210. The second web 210 may be a transparent thermally stable material, such as a coated or laminated polyethylene therephthalate. The pouch has a pair of heat seals 212 extending along the opposed side margins and a bottom heat seal structure 215. Opposite the bottom heat seal structure 215, the pouch has an opening defined by the first web straight end edge 251 and the second web 210 straight end edge 252. An adhesive 217 is provided in a strip-like configuration on the back or outer surface of the first web 211 parallel with, and spaced from, the first web straight end edge 251. Typically, the adhesive is initially covered with a conventional release paper (not illustrated).

As best illustrated in FIGS. 4B and 4C, the adhesive strip 217 has a top edge 261 that defines a first fold line (designated "Fold Line 1" in FIGS. 4B and 4C) along the margin of the strip that is parallel to and nearest the first web straight end edge 251. The adhesive strip 217 has a bottom edge 262 defining a second fold line (designated "Fold Line 2" in FIGS. 4B and 4C) along the margin of the strip that is parallel to and furthest from the first web end edge 251.

FIG. 4C illustrates how the pouch 200 of FIGS. 4A and 4B may be folded to form a self-sealing closure. Specifically, with the pouch 200 oriented vertically as illustrated in FIG. 4B, the webs 210 and 211 are first folded together away from the first web 211 along the first fold line. Next, the webs are folded together along the second fold line. Finally, the webs are folded together for the third time along a third fold line (designated "Fold Line 3" in FIGS. 4B and 4C) which is defined as being generally in registration with the repositioned first fold line across the pouch.

After the third fold, the pouch has the configuration illustrated in FIG. 4C wherein the adhesive sealing strip 217 has become oriented against an adjacent region of the second web 210 to form a closure seal of the pouch opening. The closure seal, in combination with the folded configuration of the webs, is thus seen to provide a tortuous path or barrier against the ingress of contaminants into the pouch.

A variation of the pouch illustrated in FIGS. 4A, 4B, and 4C is illustrated in FIGS. 5A and 5B. The pouch is designated generally in FIGS. 5A and 5B by the reference numeral 600 and comprises a first web 611 and a second web 610. The webs are sealed together along the pouch side margin and along the bottom of the pouch. The composition and web construction of the pouch 600 is substantially the same as in the pouch 200 illustrated in FIG. 4A and described above with reference thereto. However, unlike the pouch 200, the pouch 600 has an adhesive sealing strip 617 located at the pouch mouth on the first web 611.

The first margin 661 of the adhesive sealing strip 617 is parallel with, and substantially in registry with, the first web end edge 651. The adhesive sealing strip 617 has a second margin 662 parallel to, and spaced inwardly from, the first web end edge 651. The strip second margin 662 defines a first fold line (designated "Fold Line 1" in FIGS. 5A and 5B). Typically, the sealing strip 617 is initially covered with a conventional release paper (not illustrated) which is removed immediately prior to closing the pouch.

FIG. 5B schematically illustrates the folding of the pouch 600 to effect a closure. Specifically, the webs 611 and 610 are initially folded together away from the first web 611 along the first fold line. Then, the webs are folded along a second fold line (designated "Fold Line 2" in FIGS. 5A and 5B) which is in registry with the folded over end edges of the webs 611 and 610. This orients the adhesive sealing strip 617 against an adjacent region of the second web 610 to form a closure seal in the pouch.

Another embodiment of a self-sealing, closable pouch 700 is illustrated in FIGS. 6A and 6B. The pouch 700 has a basic web structure similar to that of pouch 200 illustrated in FIG. 4A and described above with reference thereto. The pouch 700 has a first web 711 that is sealed along the lateral edges and bottom edge to a second web 710.

The open end of the pouch 700 is defined by at least one generally straight end edge 752 on the first web 711 and by at least one generally straight end edge 751 on the first web 711 and by at least one generally straight end edge 752 on the second web 710. The generally straight end edge 752 on the second web 710 is substantially parallel to, and in registry with, the first web end edge 751. The webs 710 and 711 are unsecured along the end edges 751 and 752 to provide an open mouth for the pouch.

An adhesive sealing strip 717 is provided on the outer surface of the first web 711. The strip 717 is parallel with, and spaced from, the first web end edge 751. The strip 717 has an upper margin 761 and a lower margin 762. The spacing between the first web end edge 751 and an adhesive strip margin 761 nearest the first web end edge 751 is substantially equal to twice the width of the strip 717. Typically, a release paper (not illustrated) initially covers the adhesive strip 717.

For purposes of effecting a closure of the open end of the pouch 700, a first fold line 1 and a second fold line 2 are defined across the pouch. Specifically, the first fold line 1 is parallel to the adhesive sealing strip 717 and is located midway between the first web one end edge 751 and the adhesive strip margin 761 nearest the first web end edge 751. The second fold line 2 is defined along, or is coincident with, the adhesive strip margin 761 that is parallel to, and nearest, the first web end edge 751.

To effect the self-closure seal of the pouch 700, the corners of the pouch are folded as illustrated in FIG. 6B at about a 45 degree angle so that a portion of each pouch side edge is parallel to, and in registry with, the first fold line 1.

Next, the pouch webs 710 and 711 are folded together away from the second web 710 along the first fold line 1. Subsequently, the pouch is then folded along the second fold line 2 to orient a portion of the second web 710 against the adhesive sealing strip 717 to form the closure seal in the pouch.

FIGS. 7A and 7B schematically illustrate a method of making the prior invention pouch 100 illustrated in FIG. 2A and discussed above. Specifically, the material forming the first web 111 of each pouch is fed from a supply roll in a continuous web or sheet 111A along a path. A second web or sheet 112A is fed from a supply roll along the same path adjacent the first sheet 111A. The second sheet 112A is narrower than the first sheet 111A and the two sheets are fed together with their edges in registry along one side so that a portion of the first sheet 111A extends outwardly on the opposite side to form the pouch flaps 118 (FIG. 2A) at the pouch openings.

The two webs or sheets 111A and 112A are sealed together by suitable conventional heat sealing apparatus 150. To this end, the feeding movement of the two webs may be interrupted on a periodic basis while the heat sealing apparatus 150 is engaged to form the heat sealed edges of one or more pouches. In the embodiment illustrated in FIGS. 7A and 7B, the heat seal apparatus 150 forms the heat seals for only one pouch at a time.

In the method illustrated in FIGS. 7A and 7B, a continuous strip of adhesive 117A is provided for closing the pouches. The adhesive 117A is typically carried on a continuous strip of release paper 116B. The adhesive coated release paper 116B is fed along the path in registry with the edge of the extending portion of the first web 111A and is secured, as with roller 26 to the sheet 111A.

At a station downstream of the point where the tape is applied to the sheets, the assembly of sheets and tape is transversely cut by a suitable conventional cutter apparatus 160. As best illustrated in FIG. 7B, the assembly is cut between adjacent pouches to provide the separated, individual pouches with the self-sealing closure strip structure (the finished product being the pouches 100 which are illustrated in plan view in FIG. 7B and in perspective view in FIG. 2A).

The above described method can also be used, with obvious modifications, to fabricate the pouches illustrated in FIGS. 4A-4C, 5A and 5B, and 6A-6C.

FIGS. 12A, 12B and 12C illustrate a commercially available sealing device 900 for a pouch 910 in which the end edges of the pouch webs are in registry at the pouch opening. The sealing device 900 includes a carrier strip or carrier member 902, an adhesive 904 on the carrier member 902, and split release papers 906 and 908 carried by the adhesive 904.

The sealing device 900 has a generally strip-like configuration and a length that is greater than the width of the pouch that is ultimately to be sealed with the device. The release strips 906 and 908 are of the conventional release paper composition and each may be pulled away from the adhesive 904 without causing the adhesive 904 to be removed from the carrier strip 902. The two release papers are of substantially identical width and length and may be separately and independently removed from the adhesive 904.

FIG. 12B illustrates the application of the closure device 900 to the open end of a pouch 910. Initially, the lower or bottom release paper 906 is removed to expose the adhesive 904. Then the device 900 is placed as illustrated at the open end of the pouch 910 against one side of the pouch with opposite ends of the strip-like device 900 extending beyond the lateral edges of the pouch. The pouch and sealing device are then pressed together so that the adhesive 904 secures the device 900 to one side of the pouch 910 at the open end of the pouch. When this procedure is properly effected, the pouch 910 and sealing device 900 have the configuration illustrated in FIG. 12B.

Next, the upper release paper 908 is removed from the sealing device 900 and the device 900 is folded over the open end of the pouch and secured to the other surface of the pouch. The end portions of the device 900 that extend beyond the lateral edges of the pouch can then squeezed together so as to provide a seal at each corner of the pouch.

DESCRIPTION OF THE PREFERRED EMBODIMENTS

While this invention is susceptible of embodiment in many different forms, there are shown in the drawings and will herein be described in detail preferred embodiments of the invention. It should be understood, however, that the present disclosure is to be considered as an exemplification of the principles of the invention and is not intended to limit the invention to the embodiments illustrated.

The precise shapes and sizes of the components herein described are not essential to the invention unless otherwise illustrated.

For ease of description, the various pouches will be described in a particular orientation and terms such as upper, lower, horizontal, etc., will be used with reference to this orientation. It will be understood, however, that the pouches in accordance with the teachings of this invention may be manufactured, stored, transported, used and sold in an orientation other than the orientation described.

The pouches may be fabricated from various suitable materials and it is not intended to limit the invention to the materials set forth with reference to the preferred embodiments.

A novel pouch structure in accordance with the teachings of the present invention is illustrated in FIGS. 8A, 8B, 8C and 8D and is designated generally therein by the reference numeral 800. The pouch 800 has an opposing web structure similar to the web structure of the prior invention pouches described above.

Basically, the pouch 800 has a first or top web 801 and a bottom or base web 802. The first web 801 may be a transparent thermally stable material, such as a coated or laminated polyethylene terephthalate or such as a polypropylene film. The second web 802 may be a stream or gas permeable paper material that permits the pouch to undergo sterilization. Alternatively, the first web 801 may be a steam or gas permeable paper material that permits the pouch to undergo sterilization while the second web 802 may be a transparent thermally stable material, such as a coated or laminated polyethylene terephthalate or such as a polypropylene film.

The first and second webs are sealed together at least partially around an interior portion of the webs by suitable heat seals 804. As best illustrated in FIG. 8B, the first web 801 has at least one generally straight end edge 808 defining part of the pouch opening and the second web 802 has at least one generally straight end edge 810 oriented generally parallel to, and in registry, with, the first web one end edge 808. The second web 802 is not secured along its end edge 810 to the first web so as to define the pouch opening.

A sealing strip 812 extends across the pouch 800. The sealing strip includes, as best illustrated in FIG. 8B, a carrier strip or carrier member 816 that has a first portion 818 secured to the first web 801 and a second portion 820 that is initially unsecured to the web 801. The first portion 818 of the carrier member 816 is secured to the first web 801 with an adhering means or adhesive 822 which covers one surface of the carrier member 816 on the first portion 818 and which also extends over the surface of the second portion 820 of the cover member 816. The carrier member 816 may be a film such as nylon or the product sold under the trademark Mylar.

The carrier member 812 can be bent or flexed outwardly along a line between the first and second portions 818 and 820, respectively, as best illustrated in FIGS. 8A and 8B. This bend line may be scored or marked with suitable indicia if desired. Normally, the closure sealing strip 812 will be substantially flat against the pouch until it is temporarily bent or moved outwardly during the closure folding of the pouch.

A removable cover means 826, such as a peelable release strip or release paper, is provided on the carrier member second portion 820 over the adhesive 822 for preventing the adhesive 822 from adhering to either of the webs unless and until the cover means 826 is removed. The cover strip 826 may also be a film such as nylon or the product sold under the trademark Mylar.

The sealing strip 812 is disposed on the pouch 800 a predetermined distance inwardly from the pouch opening end edges 808 and 810. A fold line 809 is defined on the portion of the pouch extending upwardly from the carrier member secured portion 818. In the embodiment illustrated, the fold line 809 is located about midway between the pouch end and the carrier member second portion 818.

When closing the pouch, the pouch open end corners are preferably folded at an angle as illustrated in FIG. 8C. Then the carrier member second portion 820 is bent or moved outwardly and the webs 801 and 802 are folded over together about the fold line as illustrated in FIG. 8D. When folded, the folded over portion of the first web 801 confronts an adjacent portion of the first web 801. The cover means or release paper 826 is of conventional design and can be peeled away from the adhering means or adhesive 822 without pulling the adhesive 822 off of the carrier member second portion 820. The carrier member second portion 820 is then secured to the back surface of the folder over second web 802 to effect the closure seal of the pouch.

The cross-sectional dimensions of the pouch and strip structure illustrated in FIGS. 8B and 8D are greatly exaggerated relative to the length of the structures for purposes of clearly showing the various elements or layers of material forming the structure. Further, the folded over top portion of the pouch in FIG. 8D is shown spaced away from the adjacent portion of the pouch.

Typically, the folded over portion would be pressed flat against the underlying portion and a relatively sharp crease would be formed in the pouch at the fold line. The surface of the first web 801 on the folded over portion of the pouch would be in contact with the adjacent surface of the first web 801. This folded and creased structure would provide an even more effective barrier or tortuous path for preventing the ingress of contaminants.

Further, it is to be realized in FIG. 8D that the cross-sectional dimension of the closure strip 812 is greatly exaggerated relative to its length. It is to be realized that in the typical pouch structure, the first web 801 is a relatively thin thermoplastic film, the second web 802 is a relatively thin steam permeable paper, the adhesive 822 is a relatively thin coating or layer of adhesive material, and the carrier member 816 is a relatively thin film or paper backing member.

A method for fabricating the pouch 800 is illustrated in FIGS. 9A and 9B. Initially, a plurality of pouches 800', without the sealing strip 812, are fabricated in the same manner as the prior invention pouch 10 described above with reference to FIGS. 1A, 1B, and 1C. After a plurality of individual pouches, each without the sealing strip, have been fabricated, they are stacked in a conventional flat article feeder 830 that is associated with a conveyor 832.

The pouches 800' are fed seriatim along a path on the conveyor 832 in side-by-side relationship with the open end of each pouch 800' oriented generally parallel with the direction of feeding movement as illustrated in FIG. 9B. A length of a cover strip or release paper 826' is fed from a supply on a roll 827 and around a guide roll 828 along the path over the pouches 800'. The length of cover strip or release paper 826' is spaced inwardly of the open edges of the pouches 800'.

Downstream of the cover strip guide roll 828 a strip of tape 816' is fed from a supply or a roll 829 around a guide roll 830 adjacent the pouches 800'. As best illustrated in FIG. 9B, the cover strip 826' has a width less than the width of the strip of tape 816'. The cover strip 826' is fed between the strip of tape 816' and the pouches 800'. One edge of the cover strip 826' is aligned with one edge of the strip of tape 816'.

The strip of tape 816' preferably includes a carrier member, such as carrier member 816 described above for the pouch 800 with reference to FIGS. 8B and 8D. Further, the strip of tape 816' includes an adhesive or adhering means, such as the adhesive 822 described above for the pouch 800 with reference to FIGS. 8B and 8D. The strip of tape 816' is fed along the path over the pouches 800' with the adhesive facing downwardly toward the pouches 800' and toward the underlying cover strip 826'.

The tape guide roll 830 is vertically positioned relative to the conveyor 832 so as to urge the strip of tape 816' and the cover strip 826' together to adhere the cover strip 826' to the strip of tape 816' and also to urge the strip of tape 816' against the pouches 800' to adhere the strip of tape 816' to the pouches 800'.

Downstream of the guide roll 830, a suitable vertically reciprocating cutter apparatus 832 is provided to sever the adhered strip of tape 816' and the cover strip 826' transversely between the pouches to produce individual pouches 800 with attached self-closure sealing strips. As can be seen in the plane view of FIG. 9B, the strip of tape 816' and the cover strip or release paper 826' form a sealing strip which is positioned inwardly from the open ends of the pouches to provide pouches having the self-closure sealing strip oriented on each pouch to accommodate the fold-over closure illustrated in FIG. 8D.

FIG. 9C illustrates a modification of the above-described method for applying self-closure sealing strips to the pouches 800'. In this modification of the method, the pouches 800' are fed serially along a conveyor 832 as described above for the method illustrated in FIGS. 9A and 9B. Also, as described above with reference to FIGS. 9A and 9B, a strip of tape 816' is fed from a supply on roll 829 around the guide roll 830 along the path over the pouches 800'.

The cover strip or release paper 826' is also fed from a supply on a roll 827 along the path over the pouches 800'. The strip 826' has a width less than that of the strip of tape 816' and is fed in registry with at least a portion of the strip of tape 816' to mask the adhesive on the strip of tape 816' relative to the pouches 800'. Further, the cover strip 826' is forced against the strip of tape 816' above the pouches 800'. To this end, a guide roll 828' is positioned adjacent the guide roll 830. The strip of tape 816' and the cover strip 826' are fed through nip of the guide rolls 830 and 828' whereby the cover strip 826' is pressed against the adhesive on the strip of tape 816' and caused to adhere thereto. As the strip of tape 816' and the adhered cover strip 826' pass around the roll 830, they are forced against the pouches 800' and the portion of the tape 816' extending beyond the cover strip 826' adheres to the pouches 800'.

After the strip of tape 816' and the cover strip 826' are secured together and to the pouches 800' as illustrated in FIG. 9C, the strips are severed transversely in the same manner as described above with respect to the method illustrated in FIGS. 9A and 9B so as to form individual pouches with attached self-closure sealing strips.

The methods described above with reference to FIGS. 9A, 9B, and 9C may be effected with a continuously moving conveyor or with an intermittently moving conveyor. The cutting mechanism may be of any suitable conventional design adapted for severing the cover strip and strip of tape with the pouches moving continuously or intermittently as the case may be.

FIGS. 10A and 10B illustrate a method for making pouches and for applying a self-closure seal to the pouches in one continuous operation. The method may be used to produce a pouch such as the pouch 800 described above with reference to FIGS. 8A, 8B, 8C and 8D.

A first web of material, such as a thermoplastic film 801' is fed from a supply on a roll 840 around a guide roll 842 and along a predetermined path. Similarly, a second web of material, such as steam permeable paper 802', is fed from a supply on a roll 844 around a guide roll 846 and along the predetermined path in registry with the first web 801'.

The web 801' and 802' are sealed together by conventional heat seal apparatus 20' at least partially around interior portions of the webs leaving at least portions of the webs unsecured along one edge to define the pouch openings. The webs 801' and 802' may be fed continuously or intermittently. The heat seal apparatus 834', and other apparatus on the line to be described hereinafter, would be of the type suitable for operation the selected continuous or intermittent web feeding.

Downstream of the heat seal apparatus 834, the strip of tape 819' and cover strip or release paper 826' are applied to the pouches. As in the method described above with reference to FIGS. 9A and 9B, the tape 816' is fed from a supply on a roll 829 and has an adhesive means or adhesive on one side that ultimately becomes oriented against the upwardly facing surface of the pouches.

Similarly, the cover strip or release paper 826' is fed from a supply on a roll 827 along the path over the webs 801' and 802'. The width of the cover strip 826' is less than the width of the strip of tape 816'. And, when forming the pouch 800 described above with reference to FIGS. 8A, 8B, 8C and 8D, the cover strip 826' is fed between the strip of tape 816' and the surface of the first web 801' with one edge of the cover strip 826' aligned with one edge of the strip of tape 816'.

The cover strip 826' is fed around a roll 828 against the surface of the first web 801' and the strip of tape 816' is fed on top of the cover strip 826' around roll 830. The strip of tape 816' is forced by the roll 830 against the cover strip 826' and the portion of the strip of tape 816' extending beyond the cover strip 826' is forced against the upwardly facing surface of the first web 801'. In this manner, the strip of tape 816' is caused to adhere to the first web 801' to form excessively interconnected pouches with self-closure seals.

Downstream of the guide roll 830, the interconnected pouches are severed by a suitable cutting apparatus 848.

The cutting apparatus 848 transversely severs the successively interconnected pouches with self-closure seals at the region between each pouch to form individual pouches 800. The cutting apparatus 848 may be of any suitable conventional type adapted to operate to sever the webs and self-closure seal while they are being fed either continuously or intermittently as may be desired.

FIGS. 11A and 11B illustrate a modification of the method for applying the self-closure seal to the pouches. The method may be used on pre-formed, separate pouches that are being serially fed along the path as illustrated for the pouches 800' in FIGS. 9A and 9B. Also, the method illustrated in FIGS. 11A and 11B may be used with serially interconnected pouches formed from a continuous first web and a continuous second web as illustrated in FIGS. 10A and 10B. In particular, FIG. 11 illustrates a pouch comprising a first web of material 801" and a second web of material 802". The two webs of material may comprise a plurality of successively interconnected pouches (as illustrated in FIG. 10B) or a separate pouch (such as the separate pouches 800' illustrated in FIG. 9A).

In any case, as the webs are fed along the path, a self-closure sealing strip 812" is applied to the upwardly facing exterior surface of the first web of material 801". The seal strip 812" includes a base tape strip or carrier member 816" fed from a supply on a roll 829" around a guide roll 830" along the path of the webs 801" and 802".

As best illustrated in FIG. 11B, the strip of tape or carrier member 816" has an adhesive or adhesive means 822" on only a portion of the width of the strip. The remaining portion of the carrier member 816" is free of adhesive.

A cover strip or release paper 826" has a width at least equal to that of the adhesive 822" and is aligned with one edge in registry with one edge of the carrier member or tape 816". As best illustrated in FIG. 11A, the carrier member 816" and cover strip 826" are fed together from the roll 829'. However, the cover strip 826" may be fed, if desired, from a separate source or supply such as in the methods described above with reference to the cover strips 826" in FIGS. 9A–10B. It is immaterial whether the cover strip 826" is fed from a roll on which the strip 826" already secured to the carrier member 816" or whether the strip 826" is fed separately adjacent the carrier member 816". In either case, the cover strip 826" must be ultimately adhered to the adhesive portion of the carrier member 816".

The portion of the carrier member 816" extending beyond the cover strip 826" is initially free of adhesive. However, in order that the self-closure sealing strip can be secured to the pouches, it is necessary that means be provided for adhering the sealing strip to the pouches. To this end, adhesive is sprayed onto the extending portion of the carrier member 816" by means of a suitable adhesive sprayer 850. The adhesive may be sprayed directly onto the carrier member 816" as illustrated for the sprayer 850 in solid line. Alternatively, the adhesive may be sprayed onto a corresponding portion of the upwardly facing surface of the first web 801" as illustrated by the sprayer 850 in dashed line. In either case, the carrier member 816" ultimately becomes adhered to the first web 801" by means of the sprayed adhesive. To this end, the carrier member 816" is urged against the first web 801" by means of roller 830".

The downstream severing operations may be effected by a suitable cutter apparatus as described above with reference to the embodiments of the method illustrated in FIGS. 9A and 9B or 10A and 10B.

FIG. 13 illustrates another embodiment of a pouch with a self-closure seal according to the teachings of the present invention. A sealing strip 1012 is provided on a first web 1001 of a pouch 1000 that comprises a first web 1001 and a second web 1002. The sealing strip 1012 has a carrier member 1016 secured with adhesive 1022 to the first web 1001.

The carrier member 1016 is secured to the first web 1001 only along a first or lower portion below a flexure or bend line 1017. A second or upper portion of the member 1016, above the closure strip bend line 1017 is not initially secured to the first web 1001. Instead, the second portion of the sealing strip 1012 is provided with a cover means or release paper 1026 which is held by the adhesive 1022 and which may be peeled away from the second portion of the sealing strip without causing the adhesive 1022 to be removed from the carrier member 1016.

When forming a closure in the pouch 1000, the pouch corners are first folded at a 45 degree angle as illustrated in FIG. 13B. Next, as illustrated in FIG. 13C, the first and second webs are folded over together about a first fold line 1019 across the webs between the pouch open end (defined by the end edges of the first and second webs) and the first portion of the carrier member 1016 that is secured to the first web 1001.

Before of after the webs are folded as illustrated in FIG. 13C, the cover member or release paper 1026 is removed from the second portion of the carrier member 1016. The carrier member 1016 is then adhesively secured to the folded portion of the second web 1002 to form a closure seal at the pouch opening.

FIG. 14 illustrates another type of pouch to which the closure seal structure may be applied in accordance with the teachings of the present invention. Specifically, the pouch 2000 includes a first web 2001 which may be a steam permeable paper and a second web 2002 which may be a thermoplastic film having a gusseted configuration. A sealing strip 2012 is provided on the first web 2001. The sealing strip 2012 has a structure and configuration identical to that disclosed for the sealing strip 1012 described above with reference to FIG. 13A. A first portion of the sealing strip 2012 is secured to the first web 2001 at a location spaced below a first fold line 2019 and is adapted to close the pouch 2000 in a manner identical to that described above with respect to the pouch 1000 illustrated in FIGS. 13A–13C.

FIGS. 15A and 15B illustrate still another embodiment of a pouch 3000 with a self-closure seal in accordance with the teachings of the present invention. The pouch 3000 comprises a first web 3001, a second web 3002 and a sealing strip 3012 comprising a carrier member 3016 carrying an adhesive 3022 and a cover strip or release paper 3026. The pouch 3000 and sealing strip 3012 are substantially identical to the pouch and sealing strip of the pouch 800 described above with reference to FIGS. 8A–8D. However, in the embodiment illustrated in FIGS. 15A and 15B the sealing strip 3012 is located below the pouch open end by an amount sufficient to accommodate two folds of the pouch to form the closure. Specifically, with reference to FIG. 15B, the webs are folded once about a first fold line 3019 and a second time about a second fold line 3021. After the release paper 3026 is removed, the sealing strip 3012 is sealingly engaged with the exterior surface of the second web 3002 to form a closure seal of the pouch opening.

FIGS. 16A and 16B illustrate still another embodiment of a pouch 4000 with a self-closure seal in accordance with the teachings of the present invention. Specifically, the pouch 4000 is provided with a structure substantially identical to the pouch 3000 described above with reference to FIG. 15A. The pouch 4000 has a first web 4001 and a second web 4002. a sealing strip 4012 is provided and has a structure substantially identical to the sealing strip 3012 described above with reference to FIG. 15A. However, in the embodiment illustrated in FIGS. 16A and 16B, the sealing stip 4012 has a first or lower portion secured to the second web 4002 rather than to the first web 4001. A second or upper portion of the sealing strip remains initially unsecured to the pouch 4000 and is covered with a suitable cover member or release paper 4026.

When it is desired to sealingly close the pouch, the pouch is folded first about a first fold line 4019 and a second time about a second fold line 4021 as illustrated in FIG. 16B. The release paper 4026 is removed from the second portion of the sealing strip 4012 and the sealing strip is then engaged with the exterior surface of the first web 4001 to form a closure seal at the pouch opening.

In the foregoing description of the pouches constructed in accordance with the teachings of the present invention (FIGS. 8A–16B), the terms "first web" and "second web" have been used. It is to be realized that these terms have been used merely for convenience in describing the various structures and that the sealing strip may be applied to either of two opposing webs forming a pouch. For example, in a pouch comprising a steam permeable paper and a thermoplastic film, the sealing strip may be secured to either the thermoplastic film or to the steam permeable paper.

The pouches fabricated in accordance with the teachings of the present invention have been illustrated with a sealing strip wherein the first and second portions have slightly different widths (e.g., first portion 818 of sealing strip 812 in FIG. 8B being slightly narrower than the second portion 820). It is to be realized however, that the first portion of the sealing strip that is initially secured to the pouch may be relatively wide compared to the second portion of the sealing strip that is initially left unsecured. Conversely, the initially unsecured portion of the sealing strip may be relatively wide and the secured portion may be relatively narrow. Also, the portions may have substantially equal widths.

It is also to be realized that the two fold pouch embodiments illustrated in FIG. 13C, FIG. 15B and FIG. 16B need not be folded with equal size folds. The first and second fold lines need not be spaced apart by a distance equal to the distance between the first fold line and the pouch end. The first fold of the pouch may be either longer or shorter than the second fold of the pouch. Whether the folds are equal or unequal, the sealing strip is initially secured to the pouch at a desired location to effect the closure of the pouch when the pouch is properly folded in a predetermined manner.

Although the sealing strip has been described and illustrated in the figures as having a cover member or release paper that is generally coextensive with the initially unattached second portion of the sealing strip, it is to be realized that the cover member may extend outwardly beyond the end of the sealing strip if desired (an example of this modified construction which may be used in all of the embodiments is illustrated in FIG. 8E for one embodiment wherein the cover member 826e is shown extending outwardly beyond the end edge of the sealing strip 816 instead of being coextensive with the initially unattached second portion of the sealing strip 816 as illustrated in FIG. 8B).

From the foregoing, it will be observed that numerous variations and modifications may be effected without departing from the true spirit and scope of the novel concept of the invention. It is to be understood that no limitation with respect to the specific structure illustrated herein is intended to be or should be inferred. It is, of course, intended to cover by the appended claims all such modifications as fall within the scope of the claims.

What is claimed is:

1. A pouch having a closable opening at one end comprising:

first and second opposing webs secured together at least partially around an interior portion of the webs;

said first web having at least one generally straight end edge defining a part of the pouch opening;

said second web having at least one generally straight end edge oriented generally parallel to and in registry with said first web one generally straight end edge and being unsecured to said first web to define part of the opening; and a sealing strip extending across said pouch and including:
- a carrier member having a first portion secured to said first web and an unsecured second portion, said carrier member defining a bend line between said first and second portions about which said second portion may be bent toward or away from said first web,
- adhesive adhering means on said second portion of said carrier member for adhering said second portion of said carrier member to at least said second web, and
- removable cover means on said carrier member second portion over said adhering means for preventing said adhering means from adhering to either of said webs unless said cover means is removed whereby said webs may be folded over together about at least one fold line across said webs between said first web one generally straight end edge and said carrier member first portion, whereby said cover means can be removed, and whereby said carrier member second portion of said sealing strip can then be adhesively secured to the folded portion of said second web to form a closure seal at said pouch opening.

2. The pouch in accordance with claim 1 in which said first web is a steam permeable paper and in which said second web is a transparent, thermally stable, laminated, thermoplastic film.

3. The pouch in accordance with claim 1 in which said carrier member is a thermoplastic film.

4. The pouch in accordance with claim 1 in which said adhering means on said second portion of said carrier member is a pressure sensitive adhesive.

5. The pouch in accordance with claim 1 in which said removable cover means is a release paper that adheres to said adhering means and which can be peeled away from said adhering means without pulling said adhering means off of said second portion of said carrier member.

6. The pouch in accordance with claim 1 in which said first web is a transparent, thermally stable, laminated, thermoplastic film and in which said second web is a gas permeable paper.

7. The pouch in accordance with claim 1 in which said first web is a steam permeable paper and in which said second web is a polyethylene terephthalate or a polypropylene film.

8. A pouch having a closable opening at one end comprising:

first and second opposing webs secured together at least partially around an interior portion of the webs;

said first web having at least one generally straight end edge defining a part of the pouch opening;

said second web having at least one generally straight end edge orientated generally parallel to and in registry with said first web one generally straight end edge and being unsecured to said first web to define part of the pouch opening;

a sealing strip having a strip-like configuration on said first web oriented to extend across said first web generally parallel with said first web one end edge, said sealing strip having a bend line extending along said sealing strip generally parallel to said first web one end edge and dividing said strip into first and second portions, said first portion of the strip extending from the bend line away from said first web one generally straight end edge and said second portion extending from the bend line toward said first web one generally straight end edge, said sealing strip comprising a carrier member having first and second portions coextensive with said sealing strip first and second portions and having a first surface adapted to face toward said first web and a non-adhesive second surface adapted to face away from said first web, said carrier member second portion carrying on said first surface an adhering means for adhering said carrier member to said second web, said sealing strip including removable cover means for covering said adhering means on said carrier member second portion to prevent adherence of said carrier member to said either of said webs unless said cover means is removed; and means securing said carrier first portion to said first web whereby said first and second webs may be folded over together about at least one fold line between said first web one generally straight end and said sealing strip bend line, whereby said cover means can be removed, and whereby said carrier member second portion can be adhesively secured to the folded portion of said second web to form a closure seal at said pouch opening.

9. A pouch having an opening at one end that is foldingly-sealed closed, said pouch comprising:

first and second opposing webs secured together at least partially around an interior portion of the web;

said first web having a configuration before said pouch is foldingly-sealed wherein at least one generally straight end edge of said first web defines a part of said pouch opening;

said second web having a configuration before said pouch is foldingly-sealed wherein at least one generally straight end edge of said second web is oriented generally parallel and in registry with said first web one generally straight end edge and wherein said second web is unsecured to said first web to define part of said pouch opening;

said first and second webs being folded over together about at least one fold line across said webs; and a sealing strip extending across said pouch and including:
- a carrier member having a first portion secured to said first web adjacent the folded portion of said webs and having a second portion adhering to a surface of the folded over portion of said second web to form a closure seal of said pouch opening.

10. The pouch in accordance with claim 9 in which said first and second webs are folded over together about said first fold line that is located between said first web one generally straight end edge and said carrier member first portion and again about a second fold line that is generally parallel to the first fold line and that is spaced between said first fold line and said carrier member first portion.

11. A sealed pouch in accordance with claim 9 in which said pouch defines generally right-angle corners adjacent said opening and in which said corners are folded on a corner fold line at an angle to said first web one end edge.

12. In a method for making pouches wherein a first web is moved along a path, wherein a second web is moved along the path in registry adjacent said first web, wherein said webs are secured together at least partially around interior portions of the webs leaving at least portions of the webs unsecured along one edge to define openings, the improvement in said method comprising the steps of:

providing a strip of tape having an adhering means on one side surface and feeding said strip of tape along said path adjacent said first web with said adhering means facing said first web;

providing a removable cover strip having a width less than the width of said strip of tape and feeding said cover strip along said path between said strip of tape and said first web with one edge of said cover strip aligned with one edge of said strip of tape;

forcing said strip of tape against both said cover strip and said first web to secure said tape to said cover strip and to said first web to form successively interconnected pouches with self-closure seals; and transversely severing the successively interconnected pouches with self-closure seals at the region between each pouch to form individual pouches.

13. The improved method of claim 12 in which said steps of feeding said cover strip and tape strip includes feeding said strips with the aligned strip edges being located between the unaligned strip edges and said one edge of said webs that define said openings.

14. In a method for making pouches wherein a first web is moved along a path, wherein a second web is moved along the path in registry with said first web, wherein said webs are secured together at least partially around interior portions of the webs leaving at least portions of the webs unsecured along one edge to define openings; the improvement in said method comprising the steps of:

providing a strip of tape having adhesive means on only a portion of the width of said strip of tape and being free of adhesive means on the remaining portion of the strip width and feeding said strip of tape along said path adjacent said first web;

providing a cover strip having a width at least equal to the width of the adhesive means on said strip of tape and feeding said cover strip with said strip of tape and said first web with said cover strip aligned to be effectively interposed between said tape adhesive means and said first web;

applying adhesive material to either said remaining portion of said tape strip width or to a portion of said first web in registry with said remaining portion of said tape strip width;

forcing said strip of tape against both said cover strip and said first web to secure said cover strip to said tape and to secure said tape to said second web to form successively interconnected pouches with self-closure seals; and transversely severing the successively interconnected pouches with self-closure seals at the region between each pouch to form individual pouches.

15. The method of continuously applying a self-closure sealing strip to a plurality of pouches having open ends, said method comprising:

feeding said pouches seriatim along a path in side-by-side relationship with the open end of each pouch oriented generally parallel with the direction of feeding movement;

providing tape with adhesive means on one side surface and feeding said tape in said path adjacent said pouches with said adhesive means facing said pouches;

providing a cover strip having a width less than the width of said tape and feeding said cover strip along said path between said tape and said pouches with one edge of said cover strip aligned with one edge of said tape;

urging said tape and said cover strip together to adhere said cover strip to said tape and also urging said tape against said pouches to adhere said tape to said pouches; and severing said adhered tape and cover strip transversely between said pouches to produce individual pouches with attached self-closure sealing strips.

16. The method of continuously applying a self-closure sealing strip to a plurality of pouches having open ends, said method comprising:

feeding said pouches seriatim along a path with the open end of each pouch oriented generally parallel with the direction of feeding movement;

providing tape with adhesive means on only a portion of the width of one side surface of said tape and being free of adhesive means on the remaining portion of the tape width and feeding said tape in said path adjacent said pouches with said adhesive means facing said pouches;

providing a cover strip having a width at least equal to the width of the adhesive means on said tape and feeding said cover strip with said tape and said pouches in an orientation to at least mask said tape adhesive means relative to said pouches;

applying adhesive to either said remaining portion of said tape or to a portion of said pouches in registry with said remaining portion of said tape;

urging said tape and said cover strip together to adhere said cover strip to said tape and also urging said tape onto said pouches to adhere said tape to said pouches; and severing both said tape and said cover strip transversely between said pouches to produce individual pouches with attached self-closure sealing strips.

17. The pouch in accordance with claim 1 in which said removable cover means is wider than said carrier member second portion so as to extend from said carrier member bend line outwardly beyond the end edge of said carrier member second portion.

18. The method in accordance with claim 14 in which said cover strip has a width greater than the width of the adhesive means on said portion of the tape strip width and in which said step of feeding said cover strip with said strip of tape includes (1) orienting a portion of the width of said cover strip in alignment with said adhesive means on said portion of the tape strip and (2) orienting the remaining portion of the width of said cover strip to extend outwardly beyond the edge of the tape strip.

19. The pouch in accordance with claim 8 in which said removable cover means is wider than said carrier member second portion so as to extend from said sealing strip bend line outwardly beyond the end edge of said carrier member second portion.

20. The method in accordance with claim 16 in which said cover strip has a width greater than the width of the adhesive means on said portion of said tape and in which said step of feeding said cover strip with said tape includes (1) orienting a portion of the width of said cover strip in alignment with said adhesive means on said portion of the width of said tape and (2) orienting the remaining portion of the width of said cover strip to extend outwardly beyond the edge of said tape.

* * * * *

UNITED STATES PATENT AND TRADEMARK OFFICE
CERTIFICATE OF CORRECTION

PATENT NO.    : 4,402,453

DATED         : September 6, 1983

INVENTOR(S)   : Joseph Regenstein, Jr.

It is certified that error appears in the above-identified patent and that said Letters Patent is hereby corrected as shown below:

Title page, column 1, line 5, the middle initial "R." should be deleted from the inventor's name.

Column 3, line 40, "is" should be --in--.

Column 10, line 18, "stream" should be --steam--.

Column 12, line 22, "plane" should be --plan--.

Column 13, line 24, "819'" should be --816'--.

Column 18, line 22, insert --adhesive-- after "an".

Column 18, line 60, insert --adjacent a bend line adhesively-- before "adhering".

Signed and Sealed this

Seventeenth Day of January 1984

[SEAL]

Attest:

GERALD J. MOSSINGHOFF

Attesting Officer

Commissioner of Patents and Trademarks